US012779243B2

(12) United States Patent
Piffaretti et al.

(10) Patent No.: US 12,779,243 B2
(45) Date of Patent: Nov. 3, 2026

(54) APPARATUS FOR PROVIDING RETINAL THERAPY, METHOD FOR TRACKING A CHANGE IN RETINAL CELLS' FUNCTIONAL MODIFICATION

(71) Applicant: Oculox Technologies SA, Muzzano (CH)

(72) Inventors: Filippo Piffaretti, Giubiasco (CH); Pascal Faure, Saint Sulpice (CH)

(73) Assignee: Oculox Technologies SA, Muzzano (CH)

( * ) Notice: Subject to any disclaimer, the term of this patent is extended or adjusted under 35 U.S.C. 154(b) by 353 days.

(21) Appl. No.: 18/238,286

(22) Filed: Aug. 25, 2023

(65) Prior Publication Data

US 2024/0066316 A1 Feb. 29, 2024

(30) Foreign Application Priority Data

Aug. 31, 2022 (EP) .................................... 22193248

(51) Int. Cl.

*A61N 5/06* (2006.01)
*A61B 3/10* (2006.01)
*A61N 5/067* (2006.01)

(52) U.S. Cl.

CPC .......... *A61N 5/0622* (2013.01); *A61B 3/1025* (2013.01); *A61N 5/067* (2021.08); *A61N 2005/0626* (2013.01); *A61N 2005/0651* (2013.01); *A61N 2005/066* (2013.01); *A61N 2005/0663* (2013.01)

(58) Field of Classification Search

CPC .................. A61N 5/0622; A61N 5/067; A61N 2005/0626; A61N 2005/0651; A61N 2005/066; A61N 2005/0663; A61B 3/1025

USPC .......................................................... 351/203

See application file for complete search history.

(56) References Cited

U.S. PATENT DOCUMENTS

2003/0179344 A1* 9/2003 Van de Velde ..... A61F 9/00821 351/200
2011/0238046 A1* 9/2011 Dick ...................... A61B 3/102 606/5
2016/0345839 A1* 12/2016 Sethuraman ............. A61B 8/48
2017/0266041 A1* 9/2017 Kim ......................... A61B 3/12
2018/0353064 A1* 12/2018 Soetikno ............ A61K 49/0071

FOREIGN PATENT DOCUMENTS

EP 3192478 A1 7/2017

* cited by examiner

*Primary Examiner* — Sharrief I Broome
(74) *Attorney, Agent, or Firm* — BLANK ROME LLP

(57) ABSTRACT

A confocal scanning laser ophthalmoscope for providing retinal therapy of an eye comprises a first light source configured to emit a treatment beam at a first wavelength to a selected area of the retina, and a retinal functional tracking means. The retinal functional tracking means comprises a broadband second light source arranged to emit light within a spectrum to the selected area of the retina, and a detector configured to analyze reflected light from the retina at the selected area. The detector is adapted to determine a change in the spectrum of the reflected light, the change comprising a change in the amplitude of light at one or more specific wavelengths. The ophthalmoscope is configured to adapt a therapeutic dose emitted by the first light source in response to the determination of such a spectral change.

15 Claims, 4 Drawing Sheets

APPARATUS FOR PROVIDING RETINAL THERAPY, METHOD FOR TRACKING A CHANGE IN RETINAL CELLS' FUNCTIONAL MODIFICATION

This application claims priority from European Application No. EP22193248 filed on 31 Aug. 2022, the contents of which are to be taken as incorporated herein by this reference.

TECHNICAL DOMAIN

The present invention concerns a confocal scanning laser ophthalmoscope suitable for providing retinal therapy and a method suitable for tracking functional modifications in retinal cells'.

The confocal scanning laser ophthalmoscope and the corresponding method enable physicians to provide a treatment of the retina comprised in an eye while optimising the therapeutic dose and reducing or avoiding the risks of overtreatment of the retina.

RELATED ART

For many years, sub-threshold retina treatments, e.g., Sub-threshold Diode Micropulse laser therapy, have been widely investigated and applied for the treatment of retinal disorders.

The state-of-the-art technique for retina laser treatment is the so-called "Selective Retina Therapy", which presents an exciting efficacy profile in a very narrow power range, close to the neuroretina damage threshold.

However, an exact automatic feedback system is required for laser treatments safely to avoid neuroretina cellular damages. A deviation of the tissue heat transfer characteristics or a small procedure error can cause overtreatment. In return, the delicate neuroretina is irremediably affected by excessive thermal stresses.

The principle of action for this therapy or treatment stems from a deadly laser insult electively delivered to the cells of the Retinal Pigmented Epithelium (RPE).

The laser pulse length is limited to a fraction of a few microseconds. This may ensure selective heat confinement within some micrometres from the primary absorption chromophore (RPE-melanin).

Beam irradiance is normally selected to favour a specific laser-tissue interaction, e.g. creating the necessary RPE cells damages or stress to induce necrosis/apoptosis while avoiding the heat waves being dispersed to adjacent more delicate cells.

Selective Retina Therapy favours the photomechanical interaction induced by the important heat gradient generating microbubbles (vaporisation and cavitation effects) close to the RPE-melanin gains.

The methods as herein outlined before can be hazardous, as they work on the borderline to the threshold deposited energies above which irreversible scotoma is induced.

Other laser treatment modalities are widely investigated or used clinically, but all these result from a historical regression.

The clinical community was firmly convinced that a morphological tissue modification was a sine qua non-condition to trigger the expected healing effect. This belief, the necessity to devitalise deficient cells to hope for the replacement, is still very rooted in the clinical community.

It is thus an objective of the present invention to provide a confocal scanning laser ophthalmoscope for providing retinal therapy and a method for detecting a functional change in retinal cells, thus eliminating at least some of the disadvantages of devices and corresponding methods known from the prior art.

It needs to be noted that the confocal scanning laser ophthalmoscope and the method as suggested is suitable for use in the therapy of retinal disorders. However, no treatment or diagnosis is indicated by the present disclosure.

SHORT DISCLOSURE OF THE INVENTION

The invention concerns a confocal scanning laser ophthalmoscope for providing retinal therapy of an eye comprising:

- a first light source configured to emit a treatment beam with a first wavelength to a selected area of the retina, whereby the retina is external to the confocal scanning laser ophthalmoscope;
- a retinal functional tracking means comprising a second light source and a detector, wherein the second light source is arranged to emit light within a spectrum to the selected area of the retina, and wherein the detector is configured to analyse reflected light by the retina at the selected area, wherein the detector is adapted to determine a change in the intensity, spectrum, and polarity of the reflected light; and wherein
- the confocal scanning laser ophthalmoscope is configured to adapt a therapeutic dose emitted by the first light source in response to the detected modifications on the of the reflected light.

The eye can be an organ of vision of a human or an animal. The eye can be external to the confocal scanning laser ophthalmoscope, preferably without being in contact with the confocal scanning laser ophthalmoscope as such.

The first light source is also known as "treatment light source". The first light source can be configured to emit a therapeutic dose of light which can be comprised in the light beam, functioning as treatment beam, whereby the term "therapeutic dose" means the emission of a dose of light, such as a treatment light pulse, that is required to elicit a desired therapeutic response in the posterior segment of the eye in the treatment of disease or ailment.

The first light source can be any sort of light source that is suitable to emit a therapeutic dose or treatment beam with a specific wavelength. A broadband light source, such as a xenon lamp in combination with an optical filter, for allowing one specific wavelength only can be used as a light source. Preferably, a laser diode can provide the first light source, emitting only within a specific wavelength range.

The selected area can be any part of the retina. It can comprise a three-dimensional space (voxel) comprised of one specific layer of the retina, such as the choroid, the choriocapillaris, the Bruch's membrane, the pigmented layer or the inner nuclear layer, but also a three-dimensional space composed of multiple retinal layers in which the therapeutic light dose penetrates. Preferably the selected area of the retina can be the retinal pigment epithelium.

Alternatively, the selected area can comprise individual cells contained in one layer of the retina only. The said cells can be targeted all the more selective as the first light source has shallow depth of focus and presents chromophores with absorption peaking at excitation wavelength.

Instead, the area selected in the two-dimensional retinal plane can be smaller than 1 mm2, preferably smaller than 0.5 mm2, most preferably smaller than 0.25 mm2, and thereby precisely target the areas of retinal cells.

Alternatively, the treatment wavelength selected penetrates and interests a significant portion of the chorioretinal complex. The multi-layer action promotes the reaction of the totality of the tissue complex responsible for the photoreceptors' supportive functions. At the same time, a timely laser pulse protocol keeps the lateral heat diffusion contained, sparing the delicate neuroretinal layers from excessive heat. The voxel selected in the retinal tissue can be smaller than 0.5 mm3 preferably smaller than 0.3 mm2, most preferably smaller than 0.25 mm2.

The second light source can comprise a broadband light source, as it can also be used for the first light source in combination with an optical filter to allow only light within a specific spectrum of wavelengths to pass. The light emitted by the second light source or by the confocal scanning laser ophthalmoscope can also be in the form of a beam.

The light emitted by the second light source may not result in a therapeutic effect and thus has lower irradiance and radiant energy when compared to the first light source.

The confocal scanning laser ophthalmoscope and/or the first and second light sources can be configured to emit light (or beams) simultaneously. It means that the first light source can emit a treatment beam, and the second light source can emit light (or a beam) within a spectrum at the same time. Alternatively, the confocal scanning laser ophthalmoscope and/or the first and second light sources can be configured to operate asynchronously, meaning that only one source emits light (or a beam) at a specific time.

The area targeted by the light (or beam) emitted by the second light source and reflected by the retina can be the same as the area targeted by the treatment beam provided by the first light source.

The detector can be provided by a light-sensitive photodiode centred on the spectrum of light emitted by the second light source and/or light reflected by the retina.

A further means can be provided with the detector suitable to fractionise the spectrum of the received light into several wavelengths. Preferably the detector can be provided by a photo sensor in the form of an Avalanche-Photodiode-Array in combination with an optical grating to extract spectral data from the reflected light.

The detector can be adapted to determine a change in the spectrum of the reflected light. This can comprise the detection of a change in the amplitude of light in a specific wavelength or a shift in the spectrum, such as a redshift or blueshift, corresponding to an increase or decrease in the wavelengths contained in the spectrum of the reflected light.

The confocal scanning laser ophthalmoscope can be configured to adapt to the therapeutic dose emitted by the first light source. Adjusting the therapeutic dose can increase or decrease the fluence at the selected area of the retina.

The therapeutic dose can be adapted in response to the determination of a change in the spectrum of the reflected light.

A change in the spectrum may be caused by the stimulated photochemical reactions springing from the absorption of the treatment beam by the targeted cell's chromophore.

However, this is not the only known mechanism that may cause a change in the spectrum. Other mechanisms are but are not limited to molecular, cellular, and tissue avalanche biochemical reactions.

Since the treatment beam is emitted by the first light source at a specific wavelength and the therapeutic dose is varied, the general tissue interaction (photochemical and photothermal) can be precisely stimulated and controlled by the confocal scanning laser ophthalmoscope, which is an advantage over devices and methods known from the prior art.

The spectrum of the light emitted by the second light source can include light in a wavelength between 700 nm and 1400 nm, more preferably between 700 nm and 1000 nm, and most preferably between 700 nm and 900 nm. Light with wavelengths in this spectrum is also referred to as near-infrared light. Light within the same spectrum can be comprised in the beam for determining or detecting a change in the retinal cells.

The advantage of emitting light in the most preferred range of wavelength is that the detection of changes is focused on the range as specified, which can simplify the detection of specific changes in the retinal cells due to the stimulation with the treatment beam. In particular, the selected wavelength can be associated with the therapeutic effect envisaged by the stimulus with the therapeutic dose.

The light emitted by the first light source can be light of a specific wavelength selected from a range from 775 nm to 837 nm, preferably from 800 nm to 820 nm and most preferably from 808 nm to 812 nm. Preferably, but not exclusively, the wavelength of the light emitted by the first light source can account for 810 nm. The bandwidth of the wavelength as selectable can be +/−4 nm (e.g. full width at half maximum).

Light emitted by the first light source with a wavelength selected from the range from 808 nm to 812 nm can provide the advantage, that the light deeply penetrates into the tissue of the eye, whereby the treatment is not limited to the RPE only. The light in that specific wavelength also directly interacts with the choriocapillaris to have a synergic effect. By nature, the treatment beam containing light in this selected wavelength is diffusely absorbed within the chorioretinal complex. Thus, the treatment beam can insult to reach chromophores present in the RPE (melanin), in the Choriocapillaris (Hb, $HbO_2$), and the in the choroid (melanin), and more generally in all the cells of the target tissue complex (Cytochrome C Oxidase).

Alternatively, the light emitted by the first light source can be light of a specific wavelength selected from a range 785 nm to 845 nm, preferably from 805 nm to 840 nm and most preferably from 825 nm to 835 nm. Preferably, but not exclusively, the wavelength of the light emitted by the first light source can account for 830 nm. The bandwidth of the wavelength as selectable can be +/−4 nm (e.g. full width at half maximum).

The same advantage, as indicated for the wavelength selected from the 808 nm to 812 nm range, can also apply to the range between 825 nm and 835 nm. In this case, the absorption of the Cytochrome C Oxidase complex is specifically targeted.

The first light source can also be configured to emit light alternately at different wavelengths, for example, 810 nm for a first exposure duration and 830 nm for a second exposure duration.

Light within the same specific wavelength can be comprised in the treatment beam.

In one embodiment of the confocal scanning laser ophthalmoscope, according to the invention, the therapeutic dose can be characterised by at least one parameter of the first light source, including radiant power, irradiance, exposure duration, repetition intervals, and fluence or a combination thereof.

In another embodiment of the confocal scanning laser ophthalmoscope, according to the invention, the first light source can be configured to emit a plurality of consecutive light pulses within an exposure duration, wherein each light pulse can be characterised by an amplitude, a pulse period, and a pulse width. The exposure duration can correspond to the time used to treat the selected area of the retina.

The therapeutic dose can be characterised by the peak radiant power, pulse width, the number of consecutive pulses within the exposure duration, and the fluence or a combination thereof.

The pulse width of the pulses or the therapeutic dose can be less than one-half of a pulse period, preferably less than one-third of a pulse period.

Alternatively, or in addition, the pulse period can be equal to or less than 500 μs. Preferably, equal to or less than 250 μs. Alternatively or in addition, the exposure duration can be equal to or less than 500 ms. Preferably equal to or less than 250 ms.

The values as provided hereinbefore can prevent over-treatment.

In a further embodiment of the confocal scanning laser ophthalmoscope, according to the invention, the change in the spectrum of the reflected light can be caused by the treatment of retinal cells. The change in the spectrum can be detected while energising the first light source for applying a therapeutic dose.

This is advantageous as the effect on retinal cells can be observed and detected while the therapeutic dose is applied, particularly while the first light source is energised.

In another embodiment of the confocal scanning laser ophthalmoscope, according to the invention, the confocal scanning laser ophthalmoscope can comprise a control device.

The control device can be connected to the first light source and the retinal functional tracking means. The control device can be configured to control, at least one of the parameters of the first light source emitting the treatment beam in response to the determination of a change in the spectrum of the reflected light. By controlling the first light source, the treatment beam or the therapeutic dose is varied accordingly.

For example, the control device can be an electronic control device such as a microcontroller, FPGA, or a combination thereof.

The control device may feature analog and/or digital inputs and outputs and can be configured to receive analog or digital values from the detector. The control device may also be arranged to receive or send control commands from or to the first light source to control the parameter of the therapeutic dose as set out hereinbefore.

However, the functionality of the control device is not limited to the features as explained before. The control device may also set or control the operational parameters of the second light source.

The control device can be further adapted to control or set the at least one of the parameters of the first light source while the first light source emits a therapeutic dose to the retina. Alternatively, or in addition, the control device can be adapted to control or set the at least one parameter of the first light source after the emission of a therapeutic dose. This means that the emission can be paused between two consecutive treatments.

The control device can be configured to control the parameter of the first light source related to at least one treatment objective. At least one treatment objective can be characterised by the thermal, biochemical and systemic, and collective cellular activation of retinal cells or a combination thereof.

The treatment objective can be set via an input device, such as a human-machine interface, prior to the treatment. The control device automatically adapts the dose parameter in accordance with the set treatment objectives and in response to the detection of a change in the spectrum of the reflected light.

This ensures advantageously that a physician can set the treatment objective without any further intervention during the treatment using the confocal scanning laser ophthalmoscope. The treatment of the retina is performed in an automated or semi-automated way, at least over the timespan of an exposure duration.

The control device can be configured to control the power of the first light source between a minimum and a maximum value corresponding to the at least one treatment objective. The power in return can correspond to total dose delivered to the tissue (beam fluence). The minimum and a maximum value can be different for each of the at least one treatment objective.

In a further embodiment of the confocal scanning laser ophthalmoscope, according to the invention, the confocal scanning laser ophthalmoscope can comprise a lens configured to concentrate the light emitted by the first light source and the second light source. The light of the said light sources can use the lens as a common optical path between the light sources and the eye.

The need for further units of the confocal scanning laser ophthalmoscope, for instance, a second lens, can be omitted by using a common optical path shared by the said light sources. This reduced complexity and costs, which is desirable.

In a different embodiment of the confocal scanning laser ophthalmoscope, according to the invention, the retinal functional tracking means can comprise a wavelength dispersive element, such as a dispersive prism, an optical grating, suitable to extract spectra of the reflected light by the retina at the selected area.

In a further embodiment of the confocal scanning laser ophthalmoscope, according to the invention, the first wavelength (e.g. 830 nm) can be excluded from the determination by retinal functional tracking means.

This can be useful when the treatment beam is emitted and the spectrum of the reflected light is determined simultaneously. Interferences or superpositions can be avoided which may improve the sensitivity for detecting changes in the spectrum of the reflected light. The use of notch filters for filtering interferences or superpositions can be omitted, which leads to a simplification of the confocal scanning laser ophthalmoscope.

In another embodiment of the confocal scanning laser ophthalmoscope, according to the invention, the retinal functional tracking means can be configurated as an optical coherence tomograph or a confocal scanning microscope.

The invention also concerns a method for detecting a change in retinal cells' functional modification of an eye which can be stimulated by a light beam of a first light source, comprising the steps of:

Emitting a light beam with a first wavelength to a selected area of a retina;

Emitting a functional excitation beam to the selected area of the retina, wherein the measurement beam includes light within a spectrum;

Receiving reflected light from the selected area of the retina within the spectrum;

Determining a change in the spectrum of the reflected light.

The retinal cells can be comprised in an eye of a living organism (in vivo/in situ), however it is also possible that the eye is outside of a living organism (ex vivo). It should be noted that cell metabolism (for example) continues to function for several minutes or hours after the eye has been removed from a living organism. The same also applies to organisms post-mortem. The method can also be used for in vitro cultures of a organism's retina. In summary, the method thus can be flexibly applied for in vivo/in situ, ex vitro, and in vitro applications.

The change in the light spectrum can be caused by an activation of mitochondrial respiration activities of retinal cells. However, other changes in the retinal cells can also cause a change in the spectrum of the reflected light. These different causes can be considered or disregarded depending on the treatment objective.

The method is advantageous, as the response of the cells corresponding to the stimulation by the dose of light can be determined and/or observed.

The method can be performed by or on the confocal scanning laser ophthalmoscope as set out in at least one of the embodiments disclosed hereinbefore.

In one embodiment of the method, according to the invention, the method can comprise the step of adapting a parameter of a dose of light in response to the determination of a change in the spectrum of the reflected light.

In another embodiment of the method, according to the invention, the light beam and the functional excitation beam can be emitted simultaneously.

In a further embodiment of the method, according to the invention, the step of determining a change in the spectrum of the reflected light can be performed while emitting the light beam and/or applying the dose of light.

This step can be advantageous as the influence of the light beam and/or the dose of light on the retinal cells can be observed or detected while the light beam and/or the dose of light is applied to the retinal cells. This can prevent over-treatment.

Alternatively, the step of determining a change in the spectrum of the reflected light can be performed after emitting a dose of light.

This step can also be advantageous as the result of the dose of light on the retinal cells can be observed or detected after the dose of light was applied to the retinal cells.

Preferably the step of determining a change in the spectrum of the reflected light can be performed while and after emitting a light beam and/or a dose of light to retinal cells.

Confocal scanning laser ophthalmoscope, known from the prior art, can be combined or refurbished using the first light source and the retinal functional tracking means as disclosed.

Physicians can provide treatment with a device that they know well. In addition, can they visualise if the treatment provided by the confocal scanning laser ophthalmoscope was successful, as physicians may notice visible changes in the retinal cells. Effective and lasting functional changes reverts pathological structural changes characteristics of chronic degenerative pathologies.

Even though the embodiments or aspects as disclosed herein before might discuss different aspects of the invention, they may be combined individually or form a combination thereof in a confocal scanning laser ophthalmoscope when technically feasible and useful. However, they might also be considered separately when necessary.

SHORT DESCRIPTION OF THE DRAWINGS

Exemplar embodiments of the invention are disclosed in the description and illustrated by the drawings in which:

FIG. 1*a* illustrates a confocal scanning laser ophthalmoscope according to the invention schematically.

FIG. 1*b* illustrates the tissue stimulation by the treatment beam and the corresponding reaction of the cells.

EXAMPLES OF EMBODIMENTS OF THE PRESENT INVENTION

Figure 1A:
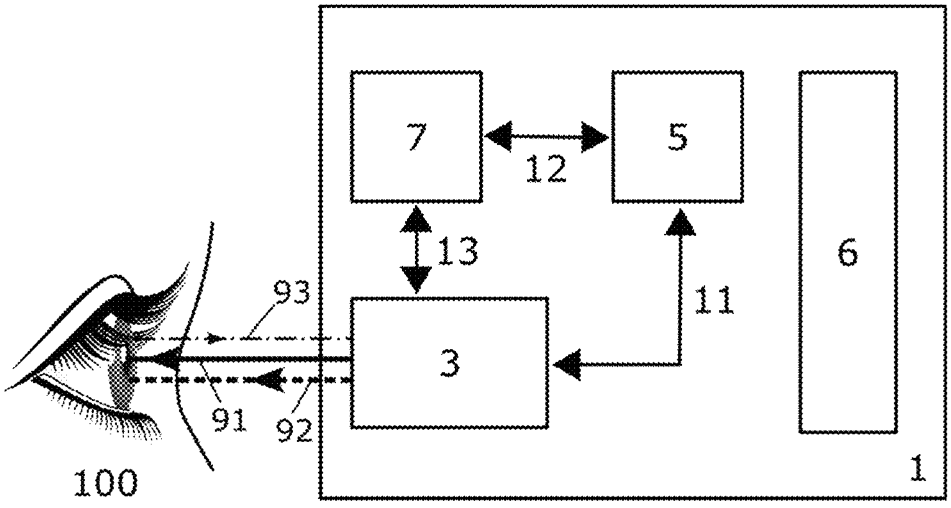

Concerning FIG. 1*a*, an example of a confocal scanning laser ophthalmoscope 1 according to the invention is illustrated. The confocal scanning laser ophthalmoscope 1 is named "apparatus" in the following.

The apparatus can be combined with or integrated into a fundus camera or another optical device typically used by physicians. However, the apparatus can also be configured as an independent, standalone device.

The apparatus 1 consists, in this example, of an optical treatment and functional tracking module 3, an optical power module 5, and a control module 7. The modules 3, 5, 7 can be placed in one common housing.

A front lens (not illustrated) of the apparatus 1 is directed towards an eye 100, whereby the optical treatment and functional tracking module 3 emit a treatment beam 91 and a functional excitation beam 92 towards the eye 100. The said lights pass through the front lens before entering the eye 100.

A portion of the functional excitation beam 92 is reflected by the retina comprised in the eye 100 and enters through the front lens of the optical treatment and functional tracking module 3 as reflected light by the retina 93. The same applies to the treatment beam 91. Some portions of the treatment beam 91 may be reflected by the by the retina 93 and may enter the of the optical treatment and functional tracking module 3 as reflected light.

The optical treatment and functional tracking module 3 determines the spectrum of the reflected light by the retina 93 and the apparatus adapts some parameters, such as the pulse width of the light pulse comprised in the treatment beam 91 in response to the detection of a change in the spectrum of the reflected light by the retina 93.

The optical power module 5 supplies the optical treatment and functional tracking module 3 with the necessary optical power to emit a treatment beam 91 to the eye 100. The optical power is transmitted from the optical power module 5 to the optical treatment and functional tracking module 3 through an optical power and communication bus 11, whereby the said bus 11 also is used for communication of operational and/or control commands parameters between the optical power module 5 and the optical treatment and functional tracking module 3.

The optical portion of the optical power and communication bus 11 is configured with an optical fiber that is suitable to conduct light without high losses.

The operation of the optical power module 5, the optical treatment and functional tracking module 3 is controlled by the control module 7. The control module 7 is communicatively connected to the said modules through communication buses 12, 13.

The control module 7 is also destined to adapt and control the emission of the treatment beam 91 in response to a change in the spectrum detected by the optical treatment and functional tracking module 3. The control module 7 directly influences the light generation in the optical power module 5.

The control module 7 can be perceived as an overarching control device, configurated to control the operation of the apparatus 1 and providing (technical) diagnostic features for all other modules 3, 5.

The apparatus 1 further comprises a human-machine interface (HMI) 6 in form of a touchscreen, touch pad and/or a keyboard. The HMI 6 is used, for instance, by an ophthalmologist to enter treatment parameters, such as treatment objectives, pupil diameters, etc.

A footswitch, as a part of the HMI 6 is used by the physician to activate the emission of the treatment beam 91 and the functional excitation beam 92.

The functionality of the modules 3, 5, 7 as herein disclosed before, is exemplified. Some of the functionalities can be combined in one module or the apparatus 1 may comprise further modules to deconcentrate the functionality further.

In a highly simplified description of the present apparatus 1 an optical-electrical feedback control is provided by the modules, in which the optical treatment unit 31, in combination with the retinal cells correspond to the system to be controlled, in which the optical functional tracking unit 32 corresponds to the sensor and in which the control module 7 corresponds to the controller.

Figure 1B:
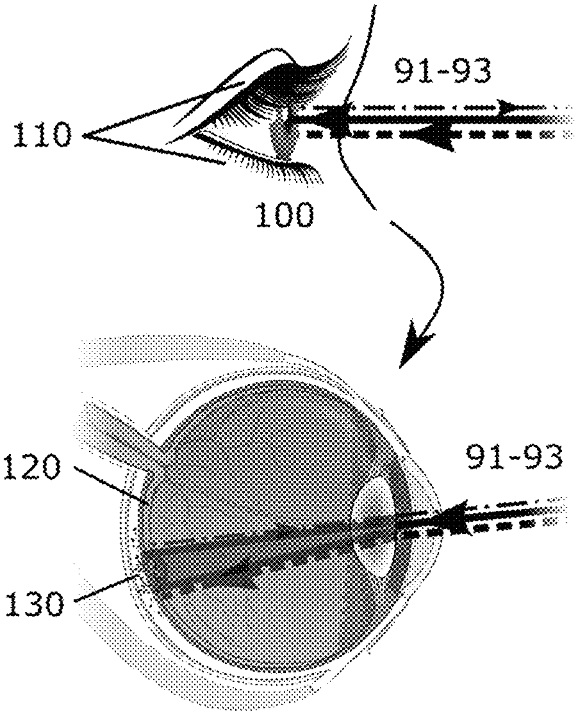

FIG. 1*b* illustrates an example of the tissue stimulation by the treatment beam and the corresponding reaction of the cells.

The treatment beam 91 and the functional excitation beam 92 are emitted in the direction of the eye 100. They enter the pupil of the eye 100 as the envelope 110 does not cover the cornea. The beams 91, 92 penetrate the eyeball and impinge on the retina 120. Portions of the beam/light of the functional excitation beam 92 are reflected by the retina 120 and reverberate in the direction of the pupil as reflected light 93. Portions of the treatment beam 91 may also be reflected by the retina 120. The reflected light 93 leaves the eyeball and enters the apparatus 1 as shown in FIG. 1*a*.

The treatment beam 91 causes a tissue stimulation 130 in the related cells. Different cells or layers of the retina may be targeted by the treatment beam 91. In reverse, the effect of the tissue stimulation 130 causes a change in the spectrum of the reflected light 93.

It needs to be noted that depending on the stimulation (intensity, duration, etc.) the spectrum may change differently. For example, a stimulation with high intensity may cause a redshift in the spectrum of the reflected light 93.

Figure 2:
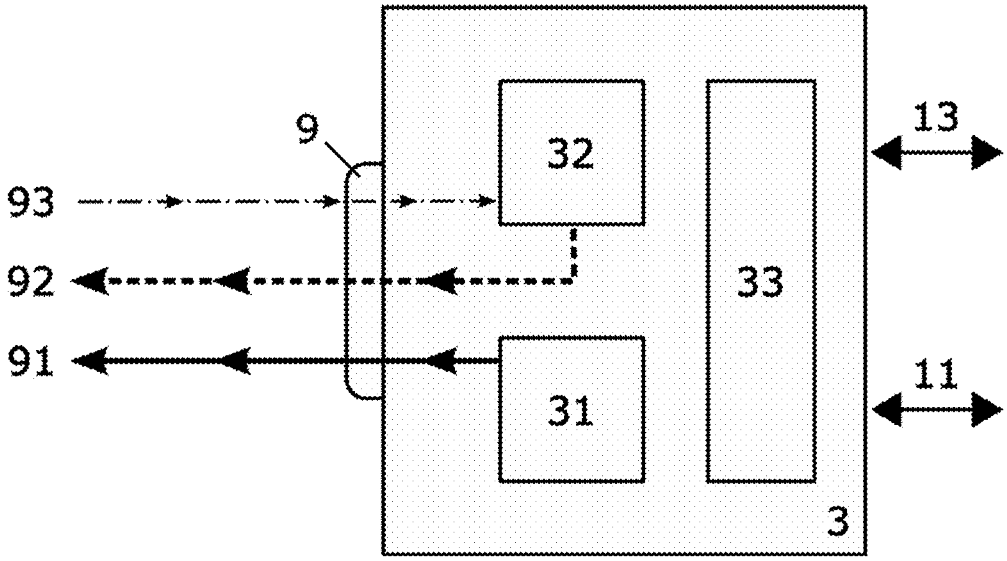
FIG. 2 illustrates an optical treatment and functional tracking optical module of the confocal scanning laser ophthalmoscope according to the invention schematically.

FIG. 2 illustrates an example of an optical treatment and functional tracking module 3 of the apparatus according to the invention.

The optical treatment and functional tracking module 3 comprises a front lens module 9, an optical treatment unit 31, optical functional tracking unit 32, and a laser beam exit module 33.

The optical treatment and functional tracking module 3 further comprises input and output ports arranged so the module can be connected to the communication bus 13 and the optical power and communication bus 11.

The optical treatment unit 31 also comprises a plurality of optical elements, such as mirrors, lens arrays and other elements for filtering light. The said optical elements are used to guide, divert, focus and/or concentrate in combination with the front lens module 9 treatment beam 91 on selected areas of the retina.

The phrase "in combination with" means in this respect that the optical path provided for the treatment beam 91 is a combination of the optical elements comprised in the optical treatment unit 31 and the front lens module 9.

The light that is focused or concentrated by the optical treatment unit 31 is provided by the laser beam exit module 33 and originates from the optical power module 5. The light emanating from the optical power module 5 is provided over the optical power and communication bus 11.

The optical functional tracking unit 32 also comprises a plurality of optical elements, such as mirrors, lens arrays and additional elements for filtering light. In addition, the optical functional tracking unit 32 includes a light source capable of providing light within a specific spectrum.

The light source used in this example for the optical functional tracking unit 32 is a near-infrared light source with wavelengths ranging between 750 nm and 980 nm.

The near-infrared light source emits the light passing through the plurality of optical elements and the front lens module 9 as functional excitation beam 92 into the direction of the eye. The retina of the eye reflects the functional excitation beam 92, whereby the light returns in the form of reflected light by the retina 93 and passes through the front lens module 9 and the plurality of optical elements comprised in the optical functional tracking unit 32.

A detector in the form of an Avalanche-Photodiode-Array (APA) and an optical grating placed in front of the sensor surface of the APA. The detector is used to extract spectral data from the reflected light by the retina and detects changes in the spectrum of the reflected light by the retina 93, while the treatment beam 91 is applied to the retina.

The treatment beam 91, the functional excitation beam 92 and the reflected light by the retina 93 share the same optical path as they pass at least through the front lens module 9 altogether.

Figure 3:
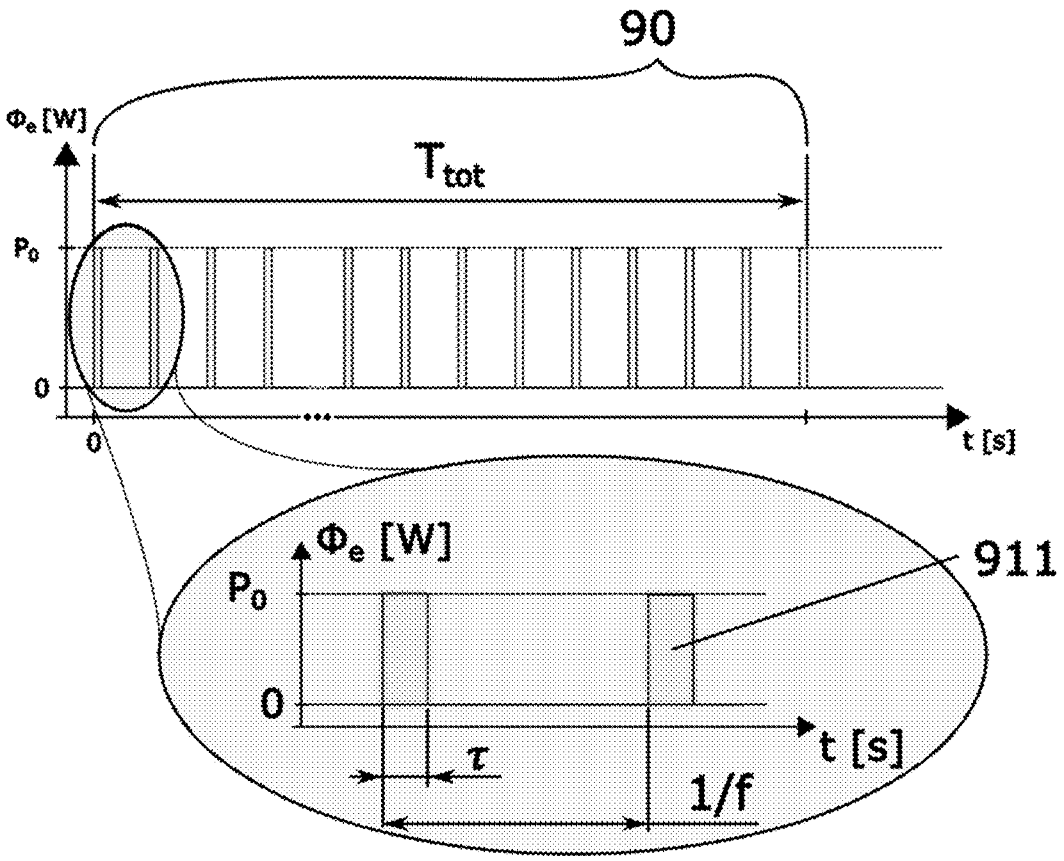
FIG. 3 shows a total therapeutic dose in the form of a repetition of light pulses schematically.

FIG. 3 illustrates an example of a total therapeutic dose 90 in the form of a repetition of treatment light pulses 911.

Light is emitted via the front lens module to the eye in the form of such a therapeutic dose 90. One therapeutic dose 90 applied to the retina can comprise in this example a plurality of periodic treatment light pulses 911. The total therapeutic dose 90 is delivered to the targeted tissues within a certain period of time, the total exposure duration $T_{tot}$.

The treatment beam 91 delivers the total therapeutic dose 90 to the targeted tissues with a pulsed protocol. The total exposure duration T tot is split into multiple pulse periods 1/*f* in which a treatment light pulse 911 is emitted. As indicated on the abscissa of the graph, the treatment light pulse 911 in each pulse period 1/*f* has a specific width corresponding to the pulse width $\tau$.

Typical values used in this example are a pulse period 1/*f* of 400 μs, a pulse width T of 100 μs, which correspond to a duty cycle of 25%, and an exposure duration T tot of 400 ms. These values result in the transmission of 1000 pulses for treatment of a selected area on the retina.

Each light pulse is characterised by a peak power amplitude $P_0$, as indicated on the ordinate of the graph. In this example accounts for the peak power amplitude $P_0$ to 40 W. The peak power amplitude $P_0$ may correspond to the radiant flux $\phi_e$ emitted by the apparatus 1.

The total therapeutic dose 90, expressed in terms of, "irradiance" x, "total exposure duration" $T_{tot}$, or fluence applied to the retina can be controlled by the amplitude of the radiated pulse $P_0$, the variation of total exposure duration $T_{tot}$, and/or the pulse width τ.

As indicated before, the total therapeutic dose 90 is adjusted in response to detecting a change in the spectrum of the reflected light by the retina.

Therefore, the values as provided before are only applicable for a stable operational point and might be subject to change during the application of the therapeutic dose 90.

Figure 4:
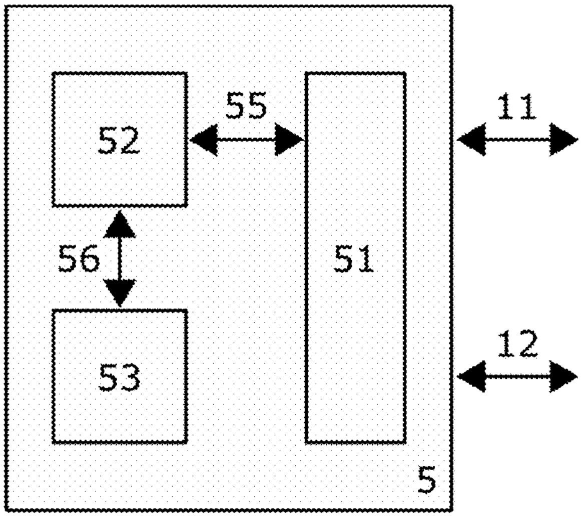
FIG. 4 illustrates an optical power module of the confocal scanning laser ophthalmoscope according to the invention schematically.

Regarding FIG. 4, an example of an optical power module 5 of the apparatus according to the invention is illustrated.

The optical power module 5 comprises a laser interface module 51, a laser control module 52 and a laser beam output module 53.

The optical power module 5 also comprises input and output ports such that the said module can be connected to the communication bus 12, and to the optical power and communication bus 11.

The laser interface module 51 comprises a power supply unit for supplying the laser control module 52 with electrical energy through the communication and electrical power supply bus 55.

The laser interface module 51 comprises a switching unit configured to interrupt or permit the supply of electrical energy to the laser control module 52. The switching unit is coupled to the footswitch of the HMI. The flow of electrical energy to the laser control module 52 is permitted if a physician activates the footswitch.

The laser control module 52 includes a light source in the form of a laser diode. The laser diode is configured to emit light with a specific wavelength, preferably with a wavelength of 810 nm or 830 nm. Due to tolerances in the manufacturing and/or during operation of the laser diode the wavelength might have a tolerance of +/−5 nm (e.g. full width at half maximum).

The laser diode is supplied with electrical energy provided by the laser interface module 51. The electrical energy is varied by a control device in the laser control module 52. The said control device controls or sets the energy that is supplied to the laser diode in a way that a pulse pattern is generated, as discussed in regards to FIG. 3 hereinbefore.

The said control device can also be connected through the communication bus 13 to the control module 7 of FIG. 1*a*. The control device receives control commands or settings from the control module 7 of FIG. 1*a* to set the pulse pattern and finally the therapeutic dose 90 in response to the detection of a change in the spectrum, which was detected by the optical functional tracking unit 32 of FIG. 2 and corresponding to a treatment objective that a physician set via the HMI of FIG. 1*a*.

However, this might not be the only possibility. The said control device might also be directly connected to the optical functional tracking unit 32 of FIG. 2, and receive commands to adapt the treatment beam 91 directly in response to detecting a change in the spectrum.

This may reduce the latency of the communication buses 12, 13 and improve the reactivity of adapting the total therapeutic dose 90.

The light which is emitted by the laser diode is transmitted to the laser beam output module 53. The laser beam output module 53 connects the light optically with the optical power and communication bus 11. The optical fiber comprised in the optical power and communication bus 11 conducts the light to the laser light input module of FIG. 2.

Figure 5:
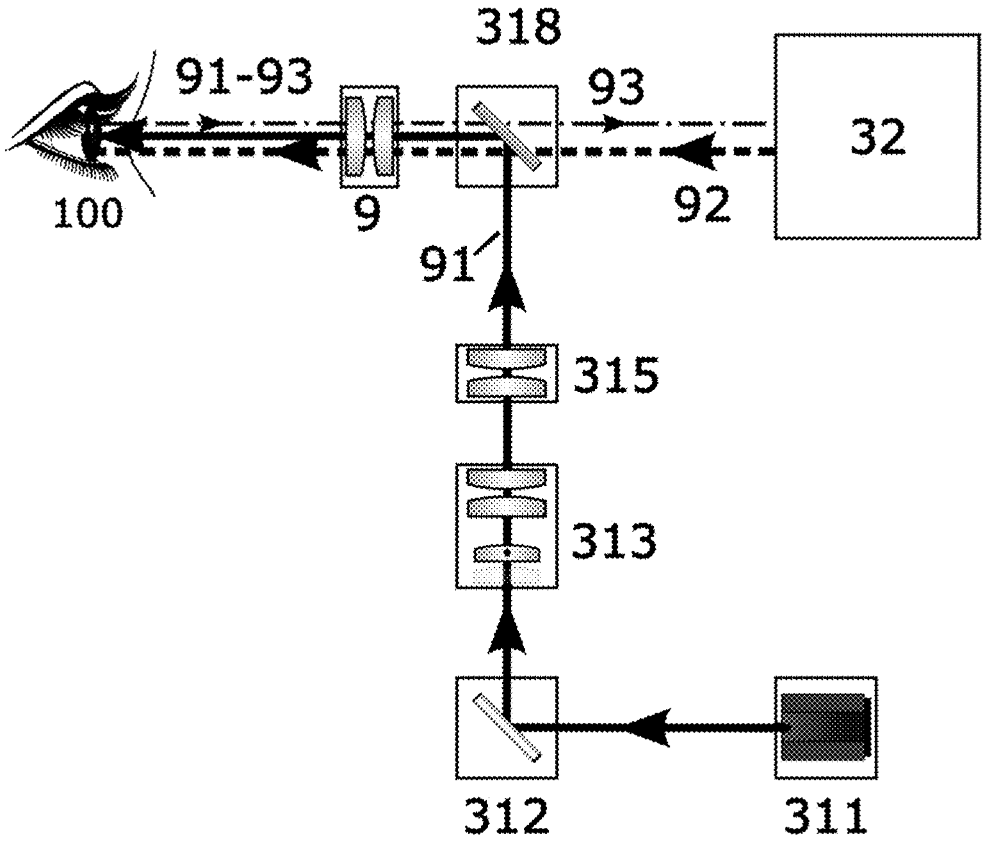
FIG. 5 shows a possible configuration of the optical treatment unit as of FIG. 2 schematically.

FIG. 5 shows an example configuration of the optical treatment unit as of FIG. 2.

In the first optical path, a treatment light source 311 generates with the use of a laser diode a treatment beam 91, having a wavelength of 830 nm.

The treatment beam 91 is redirected by an optical mirror 320 and enters the tissue layer selection 313 lens array. The said lens array 313 comprises multiple lenses, whereby at least one lens can vary its position to change the focal point (focus length) corresponding to the tissue layer which needs to be targeted.

The treatment beam 91 subsequently enters a second lens array 315 to further concentrate the treatment beam 91. Finally the treatment beam 91 arrives at the dichroic mirror 318 where it is redirected toward the front lens module 9.

The treatment light source 311, the optical mirror 312, and the lens arrays 313, 315 can be components of the optical treatment unit 31 as illustrated in FIG. 2.

The treatment beam 91 exits the front lens module 9 and is emitted into the direction of the eye 100.

In a second optical path, the optical functional tracking module 32 is energised at the same time, as the treatment light source 311 and thus emits a functional excitation beam 92 into the direction of the dichroic mirror 318. The dichroic mirror 318 directs the functional excitation beam 92 towards the front lens module 9 and exits the front lens module in the direction of the eye 100.

Portions of the functional excitation beam 92 are reflected by the retina comprised in the eye 100 and enter as reflected light by the retina 93 the front lens module 9 into the direction of the dichroic mirror 318. The reflected light by the retina 93 travels through the dichroic mirror 318 and uses the same optical path as the functional excitation beam 92.

The reflected light by the retina 93 enters the optical functional tracking unit 32, where the light i.a. is decomposed into its spectral components. The remaining functionalities are in line as explained in connection with FIG. 2.

The third optical path thus ranges between the front lens module 9 and the eye 100 and is shared by the treatment and functional excitation beam 91, 92 and the reflected light from the retina 93.

It can be noticed that the dichroic mirror 318 functions as an optical collector and deflector point, where multiple optical paths meet.

Figure 6:
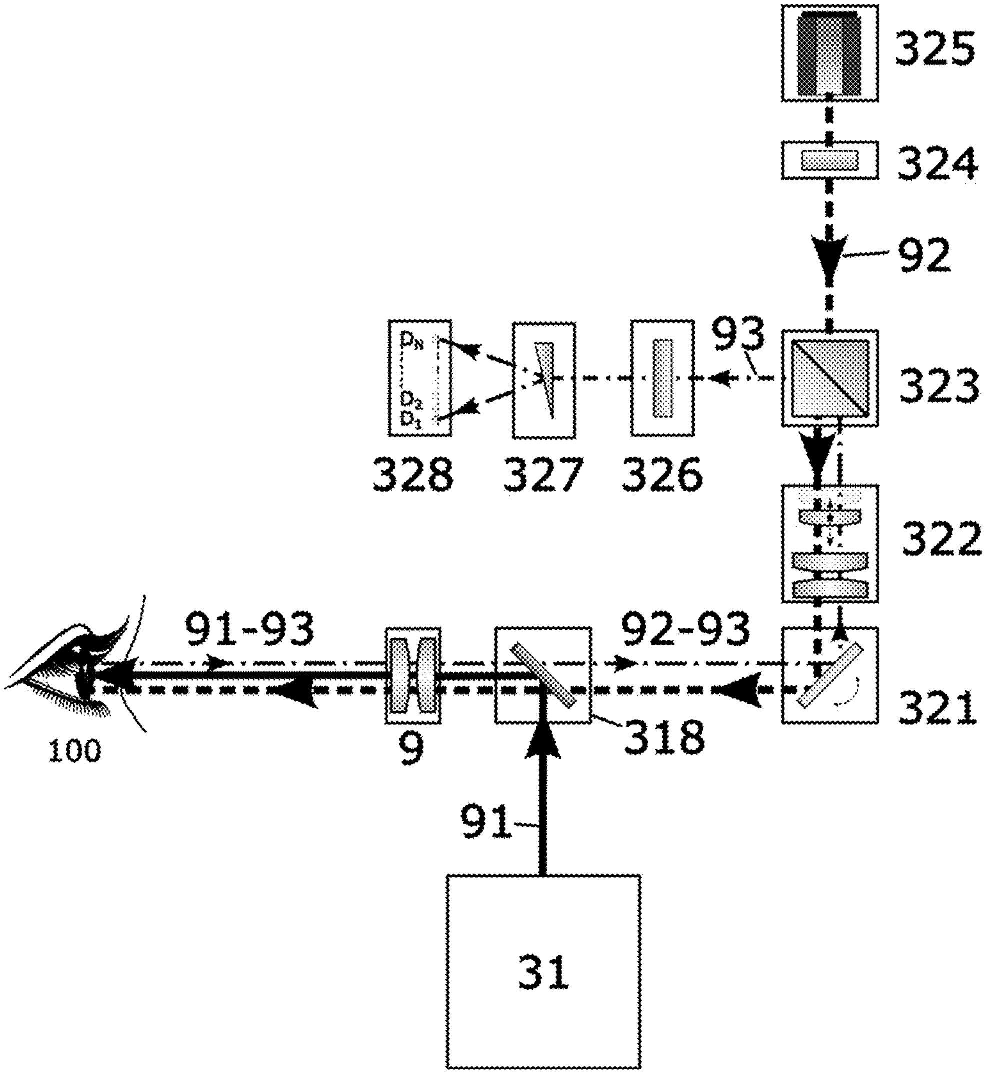
FIG. 6 illustrates a possible configuration of the optical functional tracking unit as of FIG. 4 schematically.

FIG. 6 illustrates a possible configuration of the optical functional tracking unit as of FIG. 4.

The treatment beam 91 in the first optical path is generated by the optical treatment unit 31. The optical treatment unit 31 can comprise the components as illustrated in FIG. 5. The treatment beam 91 is redirected at the dichroic mirror 318 into the direction of the front lens module 9. The treatment beam 91 exits the front lens module 9 and is emitted into the direction of the eye 100.

In a second optical path, light is generated by the broadband near infrared (NIR) light source and concentrated and/or filtered by the excitation pinhole 324 to emit the functional excitation beam 92.

The functional excitation beam 92 passes through the excitation/emission cube 323 and travels towards the tomogram selection optics 322. The tomogram selection optics 322 comprises multiple lenses, whereby at least one lens can vary its position to change the focal point (focus length) on the retina. The focal point on the retina for the functional excitation beam 92 can be the same focal point as for the treatment beam 91.

Upon leaving the tomogram selection optics 322, the functional excitation beam 92 is redirected by the 2-D scanning system 321 comprising a movable mirror. The position of the excitation beam 92 on the retina can be variably selected by changing the position of the mirror. The position or selected area on the retina of the functional excitation beam 92 and the treatment beam 91 can be exactly the same.

It is also possible that the functional excitation beam 92 targets a different position or area, which can be useful to monitor the tissue interaction of the treatment beam 91 in the environmental tissue or different layer of the retina.

The excitation beam 92 travels from the 2-D scanning system 321 to the dichroic mirror 318, whereby the dichroic mirror 318 directs the functional excitation beam 92 towards the front lens module 9 and exits the front lens module into the direction of the eye 100.

The reflected light by the retina 93 travels back through the front lens module 9, the dichroic mirror 318, the 2-D scanning system 321, the tomogram selection optics 322 and finally enters the excitation/emission cube 323, where it is redirection towards the notch filter and emission pinhole 326.

The notch filter and emission pinhole 326 can be used for stray light exclusion.

An optical dispersive grating 327 is placed in front of the line detector 328. The optical dispersive grating 327 is used to split the reflected light by the retina 93 into different wavelengths, whereby the line detector 328 captures the light level of the different wavelengths.

In conclusion, the apparatus can detect a change in the spectrum of the reflected light by the retina 93, preferably at selectable positions or areas on the retina, thanks to the 2-D scanning system.

The arrows as illustrated in all figures indicate in which direction the light travels and/or the beam is emitted or reflected.

All example embodiments present a limited selection of possible configurations of the apparatus/confocal scanning laser ophthalmoscope. However, different other configurations can solve the technical problem as set out in the initial section of this disclosure.

REFERENCE SIGNS

1 confocal scanning laser ophthalmoscope, apparatus
3 optical treatment and functional tracking module
5 optical power module
6 human machine interface (HMI)
7 control module
9 front lens module
11 optical power and communication bus
12, 13 communication bus
31 optical treatment unit
32 optical functional tracking unit
33 laser beam exit module
51 laser interface module
52 laser control module
53 laser beam output module
55 communication or control bus
56 laser light bus
90 (total) therapeutic dose—integral on light pulse envelope dose of light
91 treatment beam, light beam
92 functional excitation beam
93 reflected light by the retina while stimulated by excitation beam
100 eye
110 envelope
120 retina
130 tissue stimulation
311 treatment light source
312 optical mirror
313 tissue layer selection—treatment
315 relay lenses
318 dichroic mirror
321 2-D scanning system
322 tomogram selection optics
323 excitation/emission cube
324 excitation pinhole
325 broadband NIR light source
326 notch filter (stray light exclusion) and emission pinhole
327 optical dispersive grating
328 line detector
911 treatment light pulse
$P_0$ peak power amplitude of the radiated pulse
1/$f$ pulse period
$T_{tot}$ exposure duration
$\phi_e$ radiant flux/power
$\tau$ pulse width.

The invention claimed is:

1. A confocal scanning laser ophthalmoscope for providing retinal therapy of an eye comprising:
a first light source configured to emit a treatment beam with a first wavelength to a selected area of the retina, whereby the retina is external to the apparatus;
a retinal functional tracking means comprising a second broadband light source and a detector,
wherein the second light source is arranged to emit light within a spectrum to the selected area of the retina, and wherein the detector is configured to analyze reflected light by the retina at the selected area, wherein the detector is adapted to determine a change in the amplitude of light at one or more specific wavelengths of the reflected light; and wherein the apparatus is configured to adapt a therapeutic dose emitted by the first light source in response to the determination of a change in the spectrum of the reflected light.

2. The confocal scanning laser ophthalmoscope of claim 1, wherein the therapeutic dose comprises at least one parameter of the first light source including radiant power, irradiance, exposure duration, fluence, and/or repetition intervals.

3. The confocal scanning laser ophthalmoscope of claim 1, wherein the first light source is configured to emit a plurality of consecutive treatment light pulses within an exposure duration, wherein each treatment light pulse comprises a peak radiant power, a pulse period and a pulse width, wherein the exposure duration corresponds to the time required to conclude the treatment of the selected area of the retina.

4. The confocal scanning laser ophthalmoscope of claim 3, wherein the therapeutic dose comprises the peak radiant power, the pulse width and/or the number of consecutive pulses within the exposure duration.

5. The confocal scanning laser ophthalmoscope of claim 1, wherein the change in the spectrum of the reflected light is caused by the treatment of retinal cells while energizing the first light source for applying the therapeutic dose.

6. The confocal scanning laser ophthalmoscope of claim 1, comprising a control device connected to the first light source and the retinal functional tracking means and configured to control the at least one parameter of the first light source in response to the determination of a change in the spectrum of the reflected light.

7. The confocal scanning laser ophthalmoscope of claim 6, wherein the control device is configured to control the at least one parameter of the first light source while the first light source emits a therapeutic dose to the retina and/or after the emission of a therapeutic dose.

8. The confocal scanning laser ophthalmoscope of claim 7, wherein the control device controls the parameter of the first light source related to at least one treatment objective, wherein the at least one treatment objective comprises the thermal, biochemical and/or systemic and collective cellular activation of retinal cells.

9. The confocal scanning laser ophthalmoscope of claim 1, wherein the spectrum of the light emitted by the second light source includes light in a wavelength between 700 nm and 1400 nm, more preferably between 700 nm and 1000 nm and most preferably between 700 nm and 900 nm.

10. The confocal scanning laser ophthalmoscope of claim 1, wherein the wavelength of the light emitted by the first light source is light of a specific wavelength selected in a range from 785 nm to 845 nm, more preferably from 805 nm to 840 nm and most preferably from 825 nm to 835 nm.

11. Method for detecting a change in retinal cells' functional modification of an eye stimulated by a light beam of a first light source, comprising the steps of:

Emitting a light beam with a first wavelength to a selected area of a retina;

Emitting a functional excitation beam to the selected area of the retina, wherein the functional excitation beam includes light within a spectrum;

Receiving reflected light from the selected area of the retina within the spectrum;

Determining a change in the spectrum of the reflected light, in particular caused by an activation of mitochondrial respiration activities of retinal cells.

12. Method for detecting a change in retinal cells' of claim 11, further comprising the step of adapting a parameter of a dose of light in response to the determination of a change in the spectrum of the reflected light.

13. Method for detecting a change in retinal cells' of claim 11, wherein the light beam and the functional excitation beam are emitted simultaneously.

14. Method for detecting a change in retinal cells' of claim 11, wherein the step for determining a change in the spectrum of the reflected light is performed while and/or after emitting the dose of light.

15. Method for detecting a change in retinal cells' of claim 11, wherein the method is carried out from a confocal scanning laser ophthalmoscope.

* * * * *